United States Patent [19]

Sarkisov et al.

[11] 4,229,4:
[45] Oct. 21, 19:

[54] VACCINE FOR PROPHYLAXIS OF TRICHOPHYTOSIS IN HORSE AND METHOD OF PREPARING SAME

[75] Inventors: Arutjun K. Sarkisov; Svyatoslav V. Petrovich, both of Moscow, U.S.S.R.

[73] Assignee: Vsesojuzny Institut Experimentalnoi Veterinarii, Moscow, U.S.S.R.

[21] Appl. No.: 7,683

[22] Filed: Jan. 30, 1979

Related U.S. Application Data

[63] Continuation of Ser. No. 719,976, Sep. 2, 1976, abandoned.

[51] Int. Cl.² ............................................. A61K 39/00
[52] U.S. Cl. ..................................................... 424/88
[58] Field of Search ........................................ 424/88

[56] References Cited

FOREIGN PATENT DOCUMENTS 1307574 2/1969 U.S.S.R. .

OTHER PUBLICATIONS

Lepper Rev. Med. Vet. Mycol., vol. 6, part 9, pp. 435–446, Mar. 1969 (citing JAKSCH)—"Immunological Aspects of Dermatomycoses in Animals and Man".
V.S.P.T.O. Translation (6/77) of JAKSCH (cited in Lepper, above), "The Diagnosis of Dermatomycosis in Domestic Animals by Means of Allergic Derma Reaction", (Int. Vet. Cong. Hanover, 1963, vol. 2, pp. 1247–1250).
Petrovich Vot. Bull., 46(5), 2505, May 1976, Abstract of Veterinariya, 10:49–51, (1975), (Agents of Dermatomycosis in Horses (Trichophytum Equinum, Gypseum and Microsporium Equinum).
U.S.P.T.O. Translation, (6/77) of Petrovich Veteri riya, 10:49–51, (1975), Agents of Dermatomycosis Horses.

*Primary Examiner*—Shep K. Rose
*Attorney, Agent, or Firm*—Fleit & Jacobson

[57] ABSTRACT

The invention provides a vaccine for prophylaxis trichophytosis in the horse which comprises a susp sion of microconidia of the immunogenic strain Tricl phyton equinum in a sterile physiological salt solut: having a pH from 6.2 to 7.0, the concentration of microconidia ranging from 30 to 45 million micro nidia in 1 ml of sterile saline solution. The invention a provides a method for preparing said vaccine for p phylaxis of trichophytosis in the horse which invol growing the immunogenic culture Trichophyton ec num on a solid culture medium at a temperature of to 28° C. for 15 to 25 days until optimum amounts microconidia of said culture have accumulated, al which the resulting propagated biomass is separat homogenized to prepare a suspension of separate mic organism cells, and the end product finally isolated lyophilic drying. The use of the vaccine, prepared the inventive method, rules out trichophytosis mort ity among horses to abolish losses due to untimely s: of pedigree and sporting horses, and also prevents inf tion of man. When tested on a mass scale, the vacc proved highly efficacious (95–98%).

9 Claims, No Drawings

VACCINE FOR PROPHYLAXIS OF TRICHOPHYTOSIS IN HORSE AND METHOD OF PREPARING SAME

This is a continuation of application Ser. No. 719,976, filed Sept. 2, 1976 now abandoned.

This invention relates to a new vaccine for prophylaxis of trichophytosis in the horse and a method for preparing it.

Trichophytosis in the horse is a fungal infection caused by a species of Trichophyton. The infection is transmitted by frequent contacts of animals belonging to different epizootic zones: hippodromes, sport societies, etc., that bring the animals together in numerous contests.

Trichophytosis-affected horses are not admitted to the sporting contests and are withheld from sales. Treatment of the animals, disinfection and quarantine measures detain the animals at stud-farms and hippodromes.

Diseased animals are the source of infection of the personnel and sportsmen. The ever growing interest in equestrian sports increases the danger of spreading the infection among the population.

Measures to control the disease are usually limited by traditional local treatment of the affected sites of the skin with medical preparations, quarantines, disinfection, and also prophylactic treatment of the skin. The measures are time-consuming; yet they do not solve the problem of effective prophylaxis of trichophytosis in the horse.

The literature lacks information on the means of specific prophylaxis of trichophytosis in the horse.

The new vaccine for prophylaxis of trichophytosis in the horse comprises, according to the invention, a suspension of microconidia of the immunogenic strain Trichophyton equinum in a sterile saline solution having a pH of 6.2 to 7.0, concentration of the microconidia ranging from 30 to 45 million microconidia in 1 ml of the sterile saline solution. A saline solution, or physiological salt solution, is a 0.85% solution of sodium chloride in water. In addition to microconidia, the suspension also contains fragments of mycelium and macroconidia. All calculations of concentration, vitality of the vaccine, etc., are made with reference to the microconidia.

The vaccine is a white amorphous mass.

Vials with defective caps, as well as opened vials containing vaccine that has not been used for vaccination, should be inactivated by boiling for an hour. The preparation should be stored at a temperature from 4° to 12° C.

The vaccine is intended for prophylaxis of young and mature animals and is harmless. Active immunity to natural and artificial infection develops in the vaccinated animals toward the end of a month following vaccination. The immunity lasts for at least five years.

Vaccination of healthy animals does not cause trichophytosis in them.

According to the invention, the vaccine can be given intramuscularly for prophylaxis in a dose of 1 to 2 ml, in two injections, at a 10 to 14 day interval. The vaccine should be injected only into the third middle part of the neck. The injection site should be first disinfected.

In 7–15 days after the second vaccination, a localized crust, up to 15 mm in diameter, is formed at the injection site. The crust is spontaneously rejected in 15 to 20 days.

Vaccination of the animals during the incubati period accelerates development of the clinical manif tation of trichophytosis, but the animals would n mally recover without additional medicamentous tre ment.

Injection of double doses (compared with the p phylactic dose) to diseased animals, cures them in 15 25 days without any other treatment.

When tried on a mass scale, the vaccine proved qu effective (95–98 percent).

Prophylactic use of the vaccine practically preve trichophytosis morbidity among horses; undue expen tures for materials and labour of veterinary experts multiple medicamentous treatment and disinfecti failure in fulfillment of planned sales of pedigree a sports horses; extra keeping of trichophytosis-affec animals at studs and hippodromes; poor performance animals at studs and hippodromes; poor performanc competitions; and the danger of infecting humans.

The invention also includes a method of prepar the vaccine for prophylaxis of trichophytosis of horse, which, according to the invention, invol growing the immunogenic culture Trichophyton eq num on a solid nutrient medium, at a temperature of to 28° C., for 15 to 25 days, until optimum amounts microconidia of said culture have accumulated in medium. The procedure of determining microconi optimal amount formation is as follows. A piece of culture is taken from the matrices and placed on a sl glass. Thereafter upon adding one or two drops of tilled water thereto the piece is covered by a co glass. A preparation thus formed is looked throi under the microscope ($\times 400$).

There it must be at least 50–75 microconidia withi field of vision.

The resulting propagated biomass is then separa homogenized to prepare a suspension of separate mic organism cells, the suspension thus obtained is t dried lyophilically, and the end product isolated.

It is recommended that before lyophilic drying concentration of the obtained suspension should adjusted to 200 to 400 million microconidia in 1 ml drying medium. The preferable composition of the c ing medium is 35 to 45 percent by weight of sacchar and 5 to 7 percent by weight of gelatin in distilled wa The process for preparing the vaccine comprises following stages:

inoculation, cultivation, and accumulation of the gal mass of the culture Trichophyton equinum, hom enization of the fungal mass, standardization, fill freezing, lyophilic drying, and control of the vacc The strain Trichophyton equinum No. 1-2251 (USSR) can be used as the immunogenic cultur Trichophyton equinum. This strain is deposited at All-Union Institute of Experimental Veterinary of N cow, 109472, USSR and is available on request. strain has the following cultural, morphological, biological properties:

Cultural properties: A stab culture grown on w agar (pH 6.2–6.8) at a temperature of 26°–28° C. g rapidly developing colonies (sometimes with slightly noticeable pleats). The diameter of 20-day colony is 3–4 times greater than with the field stra A suspension culture grown on wort-agar for days, forms a snow-white film on the entire surfac the agar. The film is the mass of micro- and macr nidia.

Morphological properties: Ample micro- and r roconidia develop on wort-agar. Macroconidia are itary, consisting mainly of 2-3 segments; chlamyres are only incidental, and are practically absent. g to the presence of the mass of micro- and macidia, the washings of the culture with physiological saline solution or distilled water is a thick milky suspension.

:igenic properties: The titre of the sera of immune ls (rabbit, horses) is 1:640-1:1280 (agglutination ulent properties: When infected, the laboratory ls (guinea pigs, rabbits) and young horses, develop small foci (3-5 cm in diameter) on the 7-15th day. linic is non-manifest. In 10-20 days, the animals er without medicamentous treatment. The injection f live antigen to healthy horses does not produce il signs of trichophytosis.

nunogenic properties: Immunization of young s produces active immunity in them that can last least five years. Administration of live antigens to produces proliferation of immunologically com-: cells. The character of the reaction is first plastic and then plasmocytary. The nutrient medium owing the fungus is wort-agar, or any other nutriedium that ensures easy growth of the fungal mass ut loss of the immunogenic activity.

: inoculum is prepared by suspending lyophilically culture of the fungus in saline solution. The resultaterial is used to inoculate matrices containing nt medium. The cultivation continues for 15 to 25 it a temperature of 26° to 28° C.

: fungal mass is removed from the surface of the nt medium and transferred into a homogenizer. : water is then added and the suspension is homogl. The suspension is filled into vials, frozen, and lyophilically. It is recommended that the concen1 of the obtained suspension, before lyophilic dryould be adjusted to 200 to 400 million microcoin 1 ml of a drying medium. It is also recom:d that a solution consisting of 35 to 45 percent by t of saccharose and 5 to 7 percent by weight of 1 in distilled water should be used as the drying m. Any other medium that would ensure survival required number of viable cells after lyophilic ; can be used as the drying medium. The finished le is tested for the absence of microflora, for the ntration of live fungus cells, harmlessness, and 1ogenic potency.

a better understanding of the invention, the fol; examples of its practical embodiment are given y of illustration.

EXAMPLE 1

:ing and Using the Vaccine.

vaccine was tested on small laboratory animals orses.

experiments, carried out on 1-4 month old anihowed that active immunity is formed in them in days.

duration and active immunity were studied on 79 which were infected with virulent strains of Trichophyton 1, 2, 3, 4, 8, 12 months and 1, 3, 4, and 5 years /accination. Controls were healthy, non-immuanimals selected on the analog basis.

vaccinated animals resisted the infection while l trichophytosis foci developed in all non-vaccinated animals.

:n kept together with horses affected by trichois, the vaccinated animals remained unaffected for five years. The vaccinated horses manifested marked stability to various epizootic strains of the causative agents of trichophytosis in the horse. Commission tests of the inventive vaccine were carried out on 32 animals 6-9 months old. The animals were vaccinated and the controls were kept in the same stables without treatment. One month following the vaccination, the experimental foals were tested for stability against trichophytosis infection. Trichophyton equinum and Trichophyton mentagrophytes fungi were rubbed into scarified skin of the animals.

The test showed that 95 percent of the vaccinated animals manifested a marked resistance of the experimental infection with virulent cultures of the dermatophytes. The clear clinical picture of trichophytosis and appearance of the secondary foci of infection were observed with 100 percent of nonvaccinated animals (controls).

The next stage of the test was trial of the prophylactic efficacy of the vaccine. All newborn foals were vaccinated at a stud where trichophytosis had nested for years. During five years of observation, trichophytosis developed in only 3 out of 280 vaccinated foals. The stud became completely safe with respect to trichophytosis.

Similar measures were taken at one of the central hippodromes, where all the animals, and also all newly accepted horses were vaccinated. The total number of vaccinated horses was over three thousand animals of various breeds. Observation of the vaccinated animals showed that there was not a single case of trichophytosis among them.

The vaccine was then tried at studs, hippodromes, and sports schools, at which trichophytosis was reported. The total number of vaccinated horses was 20,000. This prevented new outbreaks of trichophytosis, and removed limitations from sales and sporting contests. The expenditures for medicamentous treatment of animals with trichophytosis and disinfection measures were thus abolished.

EXAMPLE 2

Preparing 25,000 doses of the vaccine.

The nutrient medium for growing the culture of the fungus Trichophyton equinum for the manufacture of vaccine is wort-agar. Malt-free, sterilized beer must is diluted with pure tap water to a carbohydrate content of 7 percent (after Balling) and a pH of 6.8 to 7.0. Now 2.5-3 percent by weight of agar-agar is added, the mixture is heated to dissolve the agar, and filled into 1.3-1.5 liter matrices, 300 ml of the medium in each matrix. The medium is sterilized for 40 minutes under 0.5-0.7 atmosphere pressure. The pH of the sterilized medium is usually 6.4-6.8.

The seeding material is prepared as follows: The contents of an ampoule (3-5 ml) containing dried suspension of the strain Trichophyton equinum are resuspended in 50 ml of sterile saline solution. The thus-obtained suspension is kept at room temperature for an hour, then taken into a Mohr pipette (or through a siphon), and used to inoculate the wort-agar medium in the matrices. The quantity of the inoculum is 5-7 ml of the fungus suspension per matrix. The growth of the culture can be observed visually as early as on the 3-5th day. The cultivation is continued for 15-25 days. To prepare 25,000 doses of the vaccine, 50-100 matrices with grown culture of the immunogenic strain are required. All operations are carried out in a sterile box.

The matrices with the culture are opened over the flame of a spirit burner. The biomass is taken from the surface of the nutrient medium and transferred into sterile Petri dishes. The biomass is then homogenized mechanically with distilled water (300–400 ml of distilled water for the biomass taken from 5-10 matrices). The sterile homogenizer is thereafter closed. To prevent contamination, the entire process of collecting the biomass and its transfer into the homogenizer should be carried out with a burning spirit burner. The biomass is homogenized for 15-20 minutes until a suspension of separated cells is obtained.

The homogenized fungal biomass is then transferred into flasks and saccharose-gelatin solution is added to attain the concentration of micro- and macroconidia of 200-400 million in 1 ml.

This saccharose-gelatin solution is used as a protective medium for drying. The solution is prepared by adding 4-8 percent by weight of gelatin into hot distilled water, and then (after dissolution), 10-30 percent by weight of saccharose (calculations with reference to the water taken) is added. The pH of the solution is adjusted to 7.0-7.4. The solution is then sterilized with steam for three days by 30 minute sessions, or under pressure of 0.5-0.7 atmosphere for 40 minutes. After sterilization, the pH of the solution is within 6.2-6.8.

The prepared suspension of cells is filled into sterile vials, 2 ml into each vial of 15-20 ml capacity. The vials prepared for drying are placed into refrigerating chambers at temperatures from $-50°$ to $-60°$ C. for 10-20 hours. The vials are then placed into sublimation drying apparatus. The drying is continued for 40-60 hours. In 1-3 hours, as soon as the vacuum of 9-10 mm Hg is attained, the vials are heated to $25°-40°$ C., and in 10-15 hours the temperature on the shelves of the sublimation apparatus is adjusted to $20°-25°$ C. The residual moisture content in the apparatus atmosphere should be not below 1 and not above 3 percent. The vaccine is then checked for solubility, residual moisture content, purity with respect to bacteria and moulds, concentration of microconidia, the quantity of viable cells, harmlessness, and immunogenic potency.

To determine the solubility of the vaccine, 10 ml of physiological saline solution are added into a vial containing dry vaccine. The vial contents are shaken: the vaccine should dissolve completely in 2-3 minutes.

The vaccine is tested for the absence of extraneous flora by seeding it at random onto nutrient media. Meat-peptone agar, meat-peptone broth, or the Kitt-Tarozzi medium are used for detection of extraneous bacterial flora, and Czapek medium and wort-agar are used to detect extraneous fungi. The test tubes are kept for ten days in thermostats at a temperature of $+37°$ C. and $26°$ C. All tests must show the absence of any extraneous microflora. Residual moisture content is determined by drying the vaccine under atmospheric pressure at a temperature of $100°-105°$ C. for an hour by accepted methods.

The concentration of micro- and macroconidia is determined by counting them in a special chamber for calculation of formed blood elements (Goriaev's chamber, for example).

The viability of the fungus cells is determined by suspending the vaccine in a sterile saline solution at a pH of 6.2-7.0 to restore the original volume. (If the vaccine was filled into vials in 2 ml portions, 2 ml of the saline solution should be added, if 4 ml—4 ml sould be added, etc.). A series of solutions having different concentrations from $10^{-1}$ to $10^{-8}$ is then prepared. Th material from the 6th, 7th and the 8th test tubes i seeded onto wort-agar. To determine the viability c cells, the number of survivals in 1 ml of the vaccine i the last two solutions in the series in which the fungu cells grow is counted.

The vaccine is tested for harmlessness and immuno genic potency on rabbits, guinea pigs, or on foals. Th rabbits are given 1 ml and guinea pigs 0.3–0.5 ml of th vaccine intramuscularly. The vaccine should be in th suspension form having the proper operative concentra tion.

The animals are observed for ten days. All rabbits o guinea pigs must survive. The batches of vaccine tha kill a single animal or produce complications on th injection site (abscesses, necrosis of the tissue), shoul be tested again on a doubled number of animals an checked also for the presence of extraneous flora.

If a single animal perishes or extraneous microflora i discovered in the batch, it should be rejected and ac knowledged as unfit for vaccination.

The immunogenic activity of the vaccine is tested o 7–10 month old foals. The criteria of activity are (a) th number of viable cells in 1 ml of the vaccine being no less than 200–300 million microconidia, and (b) appear ance of local reaction to vaccination on foals that i manifested by painful edema at the injection site. Th edema should appear on the 1–2nd day following th vaccination and should resolve in 3–5 days. The vaccin intended for use should be kept in a refrigerator at temperature from 4° to 12° C.

The working solution should be prepared by dissolv ing the dry vaccine in sterile saline solution having a pH 6.2–7.0 (1 ml of the dry suspension dissolved in 5 ml o saline solution). The concentration of the microconidi in the thus-prepared vaccine is 30–45 million microco nidia in 1 ml of sterile physiological saline solution.

What is claimed is:

1. A vaccine for prophylaxis of trichophytosis in th horse, comprising a suspension of microconidia of th immunogenic strain No. L-2251/70 (USSR) of Tricho phyton equinum in sterile physiological salt solution a a pH of 6.2 to 7.0, the concentration of the microconidi ranging from 30 to 45 million per 1 milliliter of th sterile physiological salt solution.

2. A method for preparing the vaccine for prophy laxis of trichophytosis in the horse defined by claim 1 comprising growing the immunogenic culture of Tri chophyton equinum on a solid nutrient medium at temperature of 26° to 28° C. for 15 to 25 days until th optimum amount of microconidia of said culture ha accumulated, separating the resulting propagated bic mass, homogenizing the biomass to prepare a suspen sion of separate cells of the microorganisms, and dryin the suspension thus obtained to isolate the end produc 3. The method according to claim 2, in which, prio to the drying, the concentration of the suspension i adjusted to 200 to 400 million microconidia per 1 millil ter of a drying medium.

4. The method according to claim 3, in which th drying medium is a solution consisting of 35 to 45 pe cent by weight of saccharose and 5 to 7 percent b weight of gelatin in distilled water.

5. The method of claim 2 in which the nutrient me dium is wort-agar.

6. A method of vaccinating a trichophytosis-fre horse to immunize it against trichophytosis, comprisin injecting a first dose of 1 to 2 milliliters of the vaccin ned by claim 1 into an injection site in the third middle part of the neck of the horse, allowing an interval of 10 to 14 days to elapse, and injecting a second dose of 1 to 2 milliliters of said vaccine into an injection in said third middle part of the neck of the horse.

A method of treating a trichophytosis-infected horse and thereafter conferring immunity against said disease in said horse, comprising injecting a first dose of 2 to 4 milliliters of the vaccine defined by claim 1 into an injection site in the third middle part of the neck of the infected horse, allowing an interval of 10 to 14 days to elapse, and injecting a second dose of 2 to 4 milliliters of said vaccine into an injection site in said third middle part of the neck of the infected horse.

8. The method according to claim 2 wherein the suspension of separate cells of the micro-organisms is lyophilically dried.

9. The method according to claim 2 wherein the nutrient medium is wort-agar, and the suspension of separate cells of the micro-organisms is lyophilically dried.

* * * * *

UNITED STATES PATENT AND TRADEMARK OFFICE
CERTIFICATE OF CORRECTION

PATENT NO. : 4,229,434
DATED : October 21, 1980
INVENTOR(S) : ARUNTJUN K. SARKISOV ET AL It is certified that error appears in the above—identified patent and that said Letters Patent is hereby corrected as shown below:

On the title page, insert

-- (30)　　Foreign Application Priority Data

September 5, 1975 Soviet Union ..........2170248 --

Signed and Sealed this

Twenty-fourth Day of March 1981

[SEAL]

Attest:

RENE D. TEGTMEYER

Attesting Officer　　　Acting Commissioner of Patents and Trademarks